_United States Patent_ [19]

Cornils et al.

[11] 4,355,192

[45] Oct. 19, 1982

[54] PROCESS FOR THE PRODUCTION OF ETHANOL AND N-PROPANOL FROM METHANOL

[75] Inventors: Boy Cornils, Dinslaken; Carl D. Frohning, Oberhausen; Gerhard Diekhaus, Oberhausen; Ernst Wiebus, Oberhausen; Helmut Bahrmann, Hünxe, all of Fed. Rep. of Germany

[73] Assignee: Ruhrchemie Aktiengesellschaft, Fed. Rep. of Germany

[21] Appl. No.: 328,984

[22] Filed: Dec. 9, 1981

[30] Foreign Application Priority Data

Dec. 10, 1980 [DE] Fed. Rep. of Germany ....... 3046481

[51] Int. Cl.$^3$ .............................................. C07C 29/00
[52] U.S. Cl. ................................................... 568/902
[58] Field of Search ......................................... 568/902

[56] References Cited

U.S. PATENT DOCUMENTS

| | | | |
|---|---|---|---|
| 3,387,043 | 6/1968 | Kuraishi et al. | 568/902 |
| 4,133,966 | 1/1979 | Pretzer et al. | 568/902 |
| 4,262,154 | 4/1981 | Gane et al. | 568/902 |

FOREIGN PATENT DOCUMENTS 2053915 2/1981 United Kingdom ............... 568/902

_Primary Examiner_—Joseph E. Evans
_Attorney, Agent, or Firm_—Jordan B. Bierman; Linda Bierman

[57] ABSTRACT

In a process for the production of ethanol and n-propanol by conversion of methanol with carbon monoxide and hydrogen in the presence of a catalyst containing cobalt, platinum, at least one halogen or halide, and an organic phosphine or phosphite, the improvement comprising the halogen or halide being chlorine or a chloride, and the phosphine or phosphite being bidentate. In addition, the conversion is carried out at pressures of 200 to 800 bars in the presence of 5 to 25% by weight of water, based on the methanol.

10 Claims, No Drawings

PROCESS FOR THE PRODUCTION OF ETHANOL AND N-PROPANOL FROM METHANOL

This application claims the priority of German No. P 30 46 481.4, filed Dec. 10, 1980.

The invention relates to a process for producing ethanol and n-propanol from methanol and synthesis gas, i.e. a mixture of carbon monoxide and hydrogen, in the presence of cobalt and ruthenium as catalysts. This reaction, which is termed homologisation, enables higher homologous alcohols to be produced starting from methanol by introducing one or more CH₂ groups.

Homologisation is attracting increasing interest since it provides a way of obtaining higher alcohols which does not depend on using petroleum. The required feedstock is synthesis gas or methanol produced therefrom; synthesis gas can be obtained for example from coal or natural gas by various technically reliable and efficient processes.

It has been known for a long time (e.g. German Patent Specification No. 867 849) to convert methanol into ethanol using hydrogen and carbon monoxide in the presence of a water-soluble cobalt catalyst at elevated temperatures and pressures. The reaction proceeds according to the following equation:

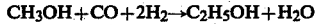

and higher alcohols may be formed in a minor amount according to the equation

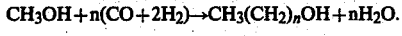

Although exclusively cobalt was originally used as catalyst for the reaction, multi-component catalysts have become increasingly important over the course of time.

U.S. Pat. No. 3,285,948 describes the production of ethanol from methanol using cobalt as catalyst, and iodine or an iodine compound as a first promoter, and a ruthenium halide or an osmium chloride as a further promoter. The claimed features are said to raise the selectivity of the reaction with respect to ethanol.

The same objective is sought according to the process of German Offenlegungsschrift No. 26 25 627 which uses a catalyst system consisting of cobalt, a halide as promoter, and a tertiary phosphine; the conversion is carried out in a hydrocarbon as solvent.

According to the teaching of U.S. Pat. No. 4,133,966, ethanol is obtained from methanol and synthesis gas using a catalyst consisting of cobalt acetyl acetonate, an organic compound of an element of Group VA of the Periodic System of the Elements, a ruthenium compound, and an iodine compound.

U.S. Pat. No. 3,285,948 discloses, inter alia, that, with platinum compounds as catalysts for the homologisation reaction, no clearly better results are obtained than with the cobalt/iodine catalyst system.

Despite the afore-described measures, the selectivity of the reaction achieved is not sufficient for commercial application. In this connection, it should be remembered that the by-products occur, not only in large amounts, but also in the form of numerous different individual compounds. Thus, in addition to the desired alcohols, there are also formed (for example) methane, ethane, propane, and various ethers, as well as methyl acetate, ethyl acetate, propyl acetate, acetaldehyde-dimethylacetal, acetaldehyde-methylethylacetal, and acetaldehyde-diethylacetal. In the industrial application of this process, a high degree of expenditure is therefore necessary in order to isolate the valuable fractions recoverable from the by-products, e.g. by hydrogenation, saponification and distillation.

Improving the selectivity of the conversion by adding a solvent to the reactants causes a considerable reduction in the conversion with respect to reactor volume and time. According to the known processes, methanol can thus be converted into higher alcohols either with a satisfactory selectivity, but low conversion, or with high conversions and a low degree of selectivity.

It is, therefore, an object of the present invention to provide a procedure for the conversion of methanol into ethanol and n-propanol with high selectivity and high conversion, and which also substantially reduces the number of by-products so that the reaction mixture can be separated in a simple manner.

The invention achieves this objective by means of reacting methanol with carbon monoxide and hydrogen at elevated pressures and temperatures of 150° to 250° C. in the presence of a catalyst containing cobalt, platinum, and at least one halogen or halide, as well as an organic phosphine or phosphite. It is characterized in that the halogen or halide is chlorine or a chloride, the organic phosphine or phosphite is bi-dentate, and the reaction is carried out at pressures of 200 to 800 bars in the presence of 5 to 25% by weight of water referred to methanol.

Cobalt is added to the reaction mixture generally in the form of a salt such as cobalt-2-ethylhexanoate, cobalt acetylacetonate, cobalt halide, cobalt nitrate, or as oxide or hydroxide. Cobalt carbonate has proved particularly suitable. It is, however, also possible to use metallic cobalt in finely divided form. Under the reaction conditions, cobalt or the cobalt compound is converted by carbon monoxide and hydrogen to form a cobalt carbonyl or cobalt hydrocarbonyl.

A further constituent of the catalyst system is platinum, which is added to the reaction mixture as a compound which dissolves in the reaction medium under the reaction conditions, e.g. a platinum halide, platinum 2-ethylhexanoate, or platinum acetylacetonate. The presence of chlorine or chloride during the reaction is essential for the process according to the invention. Chlorides, especially platinum chlorides such as $PtCl_2$, $PtCl_4$, or $H_2PtCl_6$ are preferably used.

By the term bi-dentate phosphines or phosphites, whose use is a characteristic of the new process, are understood compounds which contain two phosphorus atoms simultaneously acting as donors. As organic phosphines or phosphites that can be used within the scope of the present invention, compounds of the general formula

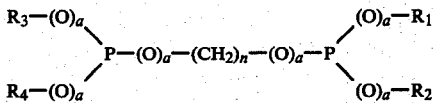

have proved particularly suitable.

In this connection, $R_1$, $R_2$, $R_3$, and $R_4$ are individually hydrogen, straight or branched chain alkyl radicals with 1 to 16 carbon atoms, or aryl radicals with 6 to 15 carbon atoms, a is 0 or 1, and n is an integer from 1 to 6. The pairs of radicals $R_1$ and $R_2$, and $R_3$ and $R_4$ may also be joined to one another and thereby form a phosphorus-containing heterocyclic ring. Such compounds are a preferred form of the present invention.

Examples of alkyl radicals are methyl, ethyl, propyl, butyl, pentyl, i-propyl, i-hexadecyl, neopentyl, of cycloalkyl radicals are cyclohexyl, dicyclopentyl, and of aryl radicals are phenyl, tolyl, naphthyl and phthalyl.

The radicals $R_1$ to $R_4$ may be joined to the phosphorus atom via oxygen atoms. Similarly, the coupling of both phosphorus atoms to the alkyl radical can be accomplished by way of oxygen atoms. Examples of compounds corresponding to the described formulae which can be employed within the scope of the present process are
(1) 1,3-bis-(monophenylphosphino)-propane
(2) 1,3-bis-(diphenylphosphino)-propane
(3) bis-(monophenylphosphino)-methane
(4) bis-(diphenylphosphino)-methane
(5) 1,3-bis-[1,3,2-dioxaphospholanyl-(2)]-propane
(6) bis-[1,3,2-dioxaphospholanyl-(2)]-methane, and
(7) 1,3-bis-(diphenoxyphosphine)-propane.

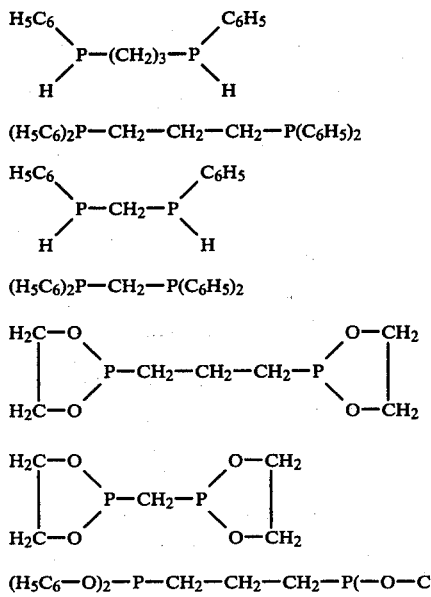

The afore-described phosphorus compounds form complex compounds with the cobalt and platinum compounds under the reaction conditions, which complexes may also contain carbon monoxide and hydrogen. These compounds form a constituent of the effective catalyst system. In addition to chlorine or chloride, the catalyst system advantageously also contains a further halogen, preferably iodine in molecular or ionic form. Alkali metal iodides and cobalt iodide may be used as the preferred iodine salts.

The catalyst system used in the process according to the invention may be added to the reaction mixture in the form of its individual constituents. Preforming of the metal complex compounds, which are components of the catalyst system, is not necessary. The catalyst system can be used repeatedly.

The carbonyl-forming catalysts and catalyst components may be suspended or dissolved in a high boiling point solvent such as diethylene glycol ether (Diglyme), tetraethylene glycol ether (Tetraglyme), neopentyl glycol (2,2-dimethyl-1,3-propanediol), ethylene glycol, tricresylphosphate, or 2-ethylhexanol. Particularly suitable as solvents or suspension agents are the organic by-products of the reaction having a higher boiling point than ethanol or n-propanol.

The methanol employed as starting material may be used in the form of the product produced in technical plants and having a water content of 4 to 6%. Additional purification is not necessary.

The original reaction mixture contains 5 to 25% by weight of water based on methanol. The addition of water inceases the conversion. Larger amounts of water have only a slight effect on the conversion, while smaller amounts have little or no effect thereon. The water is conveniently added to the reactor together with the methanol.

The molar ratio of cobalt to methanol is desirably 1:20 to 1:10,000, in particular 1:30 to 1:2000. Cobalt and phosphine or phosphite are advantageously used in a molar ratio of 1:0.1 to 1:20, preferably 1:1 to 1:5.

The atomic ratio of cobalt to platinum is 1:0.0005 to 1:1, preferably 1:0.01 to 1:0.3. Cobalt and chlorine or chloride are used in a molar ratio of 1:0.02 to 1:2, in particular 1:0.05 to 1:1. If a further halogen or halide is used, the same molar ratio of cobalt to this second halogen or halide is preferably maintained.

The carbon monoxide/hydrogen mixture should not contain any impurities such as sulfur which affect the activity of the catalyst system. Carbon dioxide and/or nitrogen in amounts of up to 5% by volume based on the total mixture are not harmful.

The new process can be carried out batchwise as well as continuously. In general, the conversion of methanol, carbon monoxide and hydrogen is carried out at temperatures of 150° to 250° C., especially 160° to 230° C. The pressure is maintained at values between 200 to 800 bars, preferably 450 to 700 bars. The molar ratio of hydrogen to carbon monoxide in the synthesis gas is 1:1 to 10:1.

The following Examples illustrate the invention.

EXAMPLE 1

6.25 moles (200 g) of methanol, 1.1 mole (19.80 g) of water, 17 mmoles (2.02 g $CoCO_3$) of Co, 6.7 mmoles (1.00 g NaI) of iodide, 22.1 mmoles (9.11 g) of 1,3-bis-(diphenylphosphino)-propane and 0.5 mmole (0.168 g $PtCl_4$) of platinum are placed in a steel autoclave (1 liter volume) equipped with a stirrer, a temperature measurement device, a sample extraction pipe, and a gas holder to collect gaseous constituents. A pressure of 550 bars is then established with synthesis gas ($CO:H_2 = 1:3$), the contents are heated to 185° C., and the reaction is continued for 6 hours while pumping in synthesis gas. After cooling the reaction mixture and releasing the pressure in the gas holder, an average sample is taken whose gas chromatography composition is given in the Table.

EXAMPLE 2

The reaction mixture occurring in Example 1 is freed from all volatile constituents by distillation and the dry residue is recycled to the reaction, as described in Example 1, together with 6.25 moles (200 g) of methanol and 1.1 mole (19.80 g) of water. A pressure of 550 bars is then established with synthesis gas ($CO:H_2 = 1:3$), the reaction mixture is heated to 185° C. and the reaction is continued for 3 hours while forcing in synthesis gas.

The sample is taken as described in Example 1, and the gas chromatography composition of the investigated sample is given in the Table.

COMPARISON EXAMPLE 1

The same procedure as set forth in Examples 1 and 2 is carried out, except that no $PtCl_4$ is added and the results are given in Tables 1 and 2. On comparing Examples 1 and 2 with the Comparison Example 1, it can be seen that the addition according to the invention of chloride in the form of $PtCl_4$ raises the conversion and selectivity of the reaction with respect to ethanol and propanol.

COMPARISON EXAMPLE 2

The procedure of Comparison Example 1 is followed, except that $PtI_2$ is used instead of $PtCl_4$. Comparing Examples 1 and 2 with the Comparison Example 2 shows that $PtCl_4$ is a particularly suitable form for adding platinum.

TABLE 1

| | GLC-Analysis (% by wt.) | | | |
|---|---|---|---|---|
| | Examples | | Comparison examples | |
| Component | 1 | 2 | 1 | 2 |
| Alkanes | 2,2 | 4,4 | 2,1 | 1,1 |
| Ethers | 3,9 | 1,6 | 3,6 | 1,8 |
| Esters | 1,2 | 2,2 | 1,1 | 0,4 |
| Acetals | 1,9 | 0,1 | 9,2 | 5,3 |
| Methanol | 44,1 | 48,2 | 67,8 | 84,5 |
| Ethanol | 40,5 | 40,3 | 12,8 | 5,6 |
| n-Propanol | 2,7 | 2,1 | 0,8 | 0,5 |
| Higher Alcohols | 1,8 | 0,7 | 0,8 | 0,3 |
| Last runnings + components | 1,7 | 0,4 | 1,8 | 0,5 |

TABLE 2

| | Example | | Comparison example | | | | |
|---|---|---|---|---|---|---|---|
| | 1 | 2 | 1 | 2 | 3 | 4 | 5 | 6 | 7 |
| Conversion referred to Methanol (in %) | 56 | 52 | 32 | 16 | | | |
| Selectivity for Ethanol (in %) | 73 | 78 | 40 | 36 | | | |
| Selectivity for Propanol (in %) | 5 | 4 | 3 | 3 | | | |

While only a limited number of specific embodiments of the foregoing invention have been expressly disclosed, it is, nonetheless, to be broadly construed and not to be limited except by the character of the claims appended hereto.

What we claim is:

1. In a process for the production of ethanol and n-propanol by conversion of methanol with carbon monoxide and hydrogen at temperatures of 150° C. to 250° C. in the presence of a catalyst containing cobalt, platinum, at least one halogen or halide, and an organic compound which is phosphine or phosphite, the improvement which comprises said halogen or halide being chlorine or a chloride, and said compound being bi-dentate, said conversion being carried out at pressures of 200 to 800 bars in the presence of 5 to 25% by weight of water, based on said methanol.

2. The process of claim 1 wherein said compound is of the formula $$R_3-(O)_a \diagdown \diagup (O)_a-R_1$$
$$P-(O)_a-(CH_2)_n-(O)_a-P$$
$$R_4-(O)_a \diagup \diagdown (O)_a-R_2$$

wherein $R_1$, $R_2$, $R_3$, and $R_4$ are individually hydrogen, straight or branched chain alkyl having 1 to 16 carbon atoms, or cycloalkyl or aryl having 6 to 15 carbon atoms, a is 0 or 1, and n is an integer from 1 to 6.

3. The process of claim 2 wherein $R_1$ and $R_2$ are joined to each other and $R_3$ and $R_4$ are joined to each other.

4. The process of claims 1, 2, or 3 wherein said halide is $PtCl_2$, $PtCl_4$, or $H_2PtCl_6$.

5. The process of claims 1, 2, or 3 wherein the molar ratio of said cobalt to said methanol is 1:20 to 1:10,000, and the molar ratio of said cobalt to said phosphine or phosphite is 1:0.1 to 1:20.

6. The process of claim 5 wherein said ratio of cobalt to methanol is 1:30 to 1:2000 and said ratio of cobalt to phosphine or phosphite is 1:1 to 1:5.

7. The process of claim 1 wherein the atomic ratio of said cobalt to said platinum is 1:0.0005 to 1:1.

8. The process of claim 7 wherein said atomic ratio is 1:0.01 to 1:0.3.

9. The process of claim 1 wherein the molar ratio of cobalt to chlorine or chloride is 1:0.02 to 1:2.0.

10. The process of claim 9 wherein the molar ratio of cobalt to chlorine or chloride is 1:0.05 to 1:1.

* * * * *